United States Patent [19]

Schildknecht

[11] Patent Number: 4,725,554

[45] Date of Patent: Feb. 16, 1988

[54] METHOD FOR MEASURING BLOOD COAGULATION TIME

[75] Inventor: Kurt Schildknecht, Rotkreuz, Switzerland

[73] Assignee: Hoffmann-La Roche Inc., Nutley, N.J.

[21] Appl. No.: 938,309

[22] Filed: Dec. 5, 1986

Related U.S. Application Data

[62] Division of Ser. No. 379,840, May 20, 1982, Pat. No. 4,659,550.

[51] Int. Cl.$^4$ ...................... G01N 21/03; G01N 33/86
[52] U.S. Cl. ........................................................ 436/69
[58] Field of Search ............... 356/39; 422/73; 436/69

[56] References Cited

U.S. PATENT DOCUMENTS

| | | |
|---|---|---|
| 3,307,392 | 3/1967 | Owen et al. |
| 3,463,614 | 8/1969 | Leslie |
| 3,486,859 | 12/1969 | Greiner et al. |
| 3,617,222 | 11/1971 | Matte |
| 3,691,017 | 9/1972 | Brown et al. |
| 3,795,451 | 3/1972 | Mailen |
| 3,861,877 | 1/1975 | Matharani et al. |
| 3,890,098 | 6/1975 | Moreno |
| 3,911,728 | 10/1975 | Fixot |
| 4,190,542 | 2/1980 | Hodgson et al. |
| 4,290,997 | 9/1981 | Suovaniemi |
| 4,338,174 | 7/1982 | Tamura |
| 4,446,577 | 5/1984 | Meyer et al. |

FOREIGN PATENT DOCUMENTS

| | | |
|---|---|---|
| 495617 | 5/1976 | Australia |
| 497987 | 1/1979 | Australia |
| 500840 | 5/1979 | Australia |
| 502781 | 8/1979 | Australia |
| 50412 | 8/1979 | Australia |
| 50413 | 8/1979 | Australia |
| 840615 | 6/1952 | Fed. Rep. of Germany |
| 2401084 | 9/1974 | Fed. Rep. of Germany |
| 7707546 | 8/1977 | Fed. Rep. of Germany |
| 1505889 | 3/1978 | United Kingdom |

OTHER PUBLICATIONS

Whitaker; Introduction to Fluid Mechanics; Prentice-Hall, Englewood Cliffs, NJ 1968, p. 334.

*Primary Examiner*—Barry S. Richman
*Assistant Examiner*—Michael S. Gzybowski
*Attorney, Agent, or Firm*—Jon S. Saxe; Bernard S. Leon; George W. Johnston

[57] ABSTRACT

Method for measuring the coagulation time of a blood sample in which a sample-reagent mixture is formed by introducing the sample and at least one reagent into a cuvette. To reduce the operating and material costs, the sample-reagent mixture is so moved in a stationary cuvette that the mixture flows back and forth around an edge projecting into the cuvette, whereby a clot forms on this edge.

5 Claims, 10 Drawing Figures

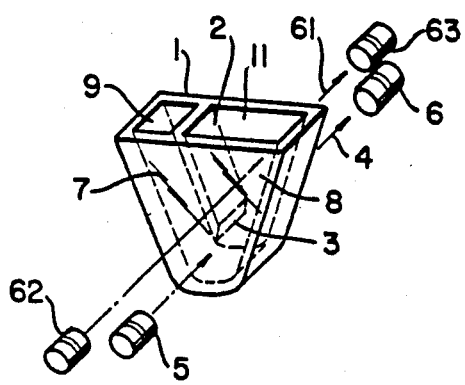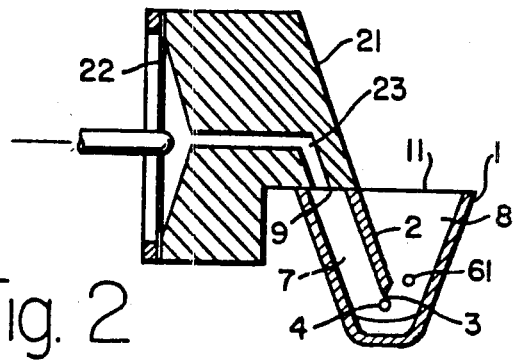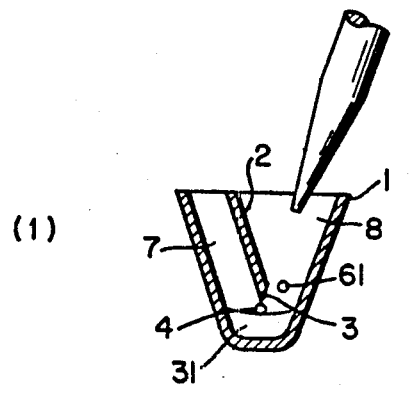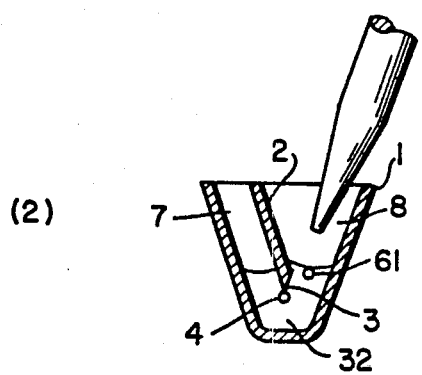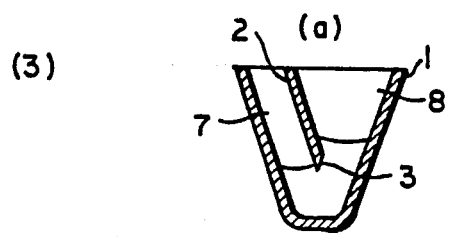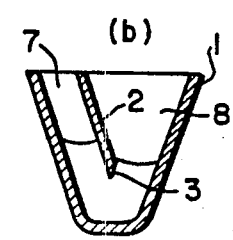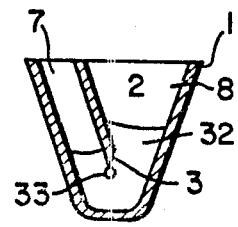
Fig. 1
Fig. 2
Fig. 3

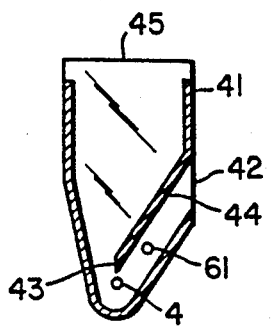
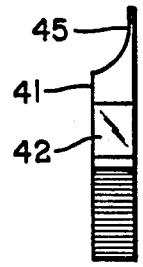
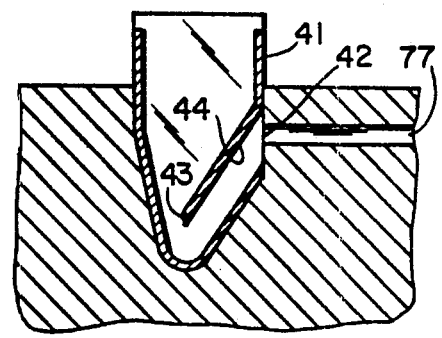
Fig. 4a  Fig. 4b  Fig. 5
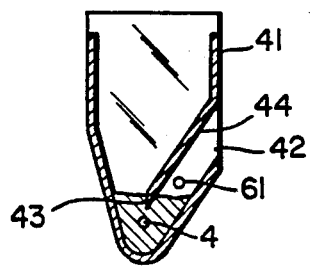
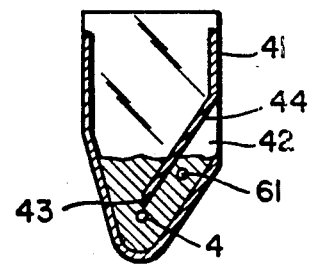
Fig. 6a  Fig. 6b
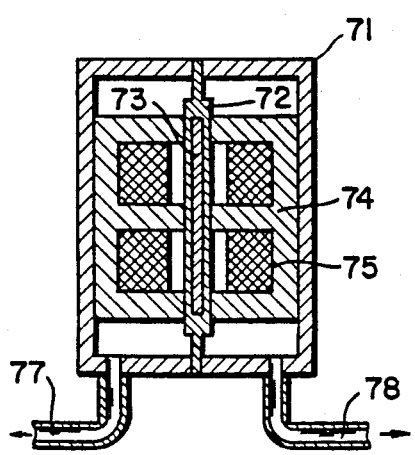
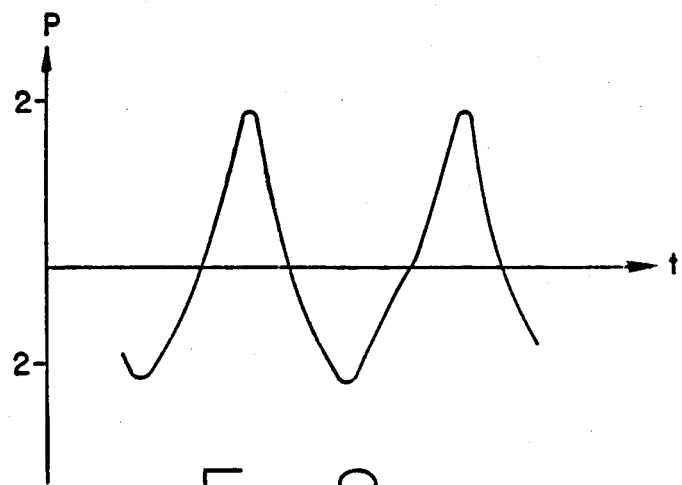
Fig. 7  Fig. 8

METHOD FOR MEASURING BLOOD COAGULATION TIME

This is a division of application Ser. No. 379,840 filed May 20, 1982, now U.S. Pat. No. 4,659,550.

BACKGROUND OF THE INVENTION

1. Field of the Invention

The invention is concerned with a method for measuring the coagulation time of a blood sample, in which a sample-reagent mixture is formed by introducing the sample and at least one reagent into a cuvette. The invention also relates to an apparatus suitable for carrying out the inventive method.

2. Description of the Prior Art

In the prior art, the coagulation time of a blood sample can be established by measuring the time it takes to form a blood clot in a sample-reagent mixture which is located in a cuvette.

German Utility Model 7707 546 illustrates a known method and an apparatus for measuring blood coagulation time. According to this Utility Model, the coagulation of a sample-reagent mixture is brought about by stirring the mixture with a stirring rod which must be introduced into a cuvette before taking measurements. The stirring rod is driven by a magnetic stirring arrangement situated outside the cuvette.

When carrying out a large number of measurements, the expenditure of work for introducing the stirring rod into the cuvette is found to be a disadvantage of the above method and apparatus. Since the magnetic stirring arrangement also constitutes a considerable portion of the total material cost of the prior art apparatus, it moreover would be desirable to have an apparatus which operates without such an arrangement.

The present invention avoids the disadvantages of the prior art by providing a method and an apparatus for measuring blood coagulation time which requires low operating and material cost.

SUMMARY OF THE INVENTION

The present invention concerns an improved method for measuring the coagulation time of a blood sample which improvement comprises moving a sample-reagent mixture in a stationary cuvette in such a way that the mixture flows back and forth around an edge projecting into the cuvette, whereby a clot forms on this edge.

The invention also concerns an apparatus for measuring blood coagulation time by utilizing the inventive method with a cuvette for receiving a sample and a reagent. In the apparatus, the upper part of the cuvette is divided into two chambers by a partition and the partition has an edge which is situated at a certain distance from the bottom of the cuvette.

In the invention, no stirring rod need be introduced into the cuvette and also no drive for such stirrer is required. The present invention therefore makes it possible to achieve a substantial reduction in the operating and material costs over the prior art devices for measuring blood coagulation time.

BRIEF DESCRIPTION OF THE DRAWINGS

Preferred embodiments of the invention are described hereinbelow with reference to the drawings wherein:

FIG. 1 is a perspective view of a cuvette and electro-optical arrangement of the present invention;

FIG. 2 is a front cross-sectional view of the cuvette and the variable air pressure arrangement of the present invention;

FIG. 3 illustrates the steps to carry out a method for measuring blood coagulation time in accordance with the present invention;

FIG. 4a is a cross-sectional front view of an alternate embodiment of a cuvette of the present invention;

FIG. 4b is an end view of the cuvette of FIG. 4a;

FIG. 5 is a cross-sectional front view of the cuvette of FIG. 4a and its connection to the variable air pressure arrangement used in the present invention;

FIG. 6a is a cross-sectional front view of the cuvette of FIG. 4a having a sample therein;

FIG. 6b is a cross-sectional front view of the cuvette of FIG. 4a having a sample-reagent mixture therein;

FIG. 7 is a cross-sectional front view of an arrangement for producing variable air pressure in accordance with the present invention; and FIG. 8 is a graph of time vs. pressure for a typical course of air pressure produced with the arrangement of FIG. 7.

DETAILED DESCRIPTION OF THE PREFERRED EMBODIMENTS

The present invention relates to an improved method and apparatus for measuring the coagulation time of a blood sample.

In an embodiment, the inventive apparatus includes a cuvette for receiving a sample-reagent mixture. The cuvette has a bottom portion and an upper portion. A partition divides the upper portion into two chambers and an edge of the partition is situated at a predetermined distance from the bottom portion of the cuvette. There is also at least one opening in the cuvette. The apparatus also includes an arrangement for producing variable air pressure in the cuvette to effect the flow of the sample reagent mixture around the edge of the partition from chamber to chamber when the mixture is at a level which is above the edge of the partition. There is also provided means for detecting the presence of the sample reagent mixture in the cuvette and means for detecting the formation of a clot on the edge of the partition.

In an embodiment of the invention, the means for determining the presence of the mixture includes a first light source for transmitting a first beam of light and a first light receiver for receiving the first beam of light. The first light source and first light receiver are located in relation to the cuvette so that the first light beam passes through the sample reagent mixture in the cuvette at a location above the edge of the partition. It is thereby possible to detect a change in the absorptance value measured with the first light beam due to the formation of the sample reagent mixture.

In an embodiment of the apparatus, the means for determining the presence of the clot includes a second light source for transmitting a second beam of light and a second light receiver for receiving the second beam of light. The second light source and second light receiver are located in relation to the cuvette so that the second light beam passes through the cuvette at a location adjacent the edge of the partition. It is thereby possible to detect a change in the absorptance value measured with the second light beam due to the formation of the clot on the edge.

In accordance with the inventive method, the respective amounts of sample and reagent introduced into the cuvette are such that the level of the resulting sample-reagent mixture in the cuvette is above the edge of the partition. Under the present invention, one detects the presence of the sample reagent mixture in the cuvette and causes the mixture to flow around the edge of the partition from chamber to chamber to form a clot on the edge. One then detects the formation of the clot. The time between the two measurements is the coagulation time.

Since the invention avoids using prior stirring rods and magnetic stirring arrangements, the invention advantageously achieves a substantial reduction in operating and material costs over the prior art.

With reference to the drawings, FIG. 1 illustrates a cuvette 1 used in an apparatus of the present invention. Cuvette 1 is made of a material (e.g. transparent plastic) which enables optical measurements to be carried out on the content within the cuvette. Cuvette 1 need not necessarily have the form shown in FIG. 1. However, it is essential that cuvette 1 has a partition 2 with a sharp edge 3 positioned at a predetermined distance from the bottom or lower portion of cuvette 1. Partition 2 separates the upper part of the cuvette into two chambers 7 and 8, respectively having openings 9 and 11.

FIG. 1 also shows a light source 5 (e.g. a light-emitting diode) and a light receiver 6 (e.g. a photodiode). With these components there is produced and, respectively, received a beam of light 4 which passes through cuvette 1 close to and below edge 3, in order to enable the measurement of the extinction of light of the cuvette content which is transversed by the beam of light 4. The path of light beam 4 through cuvette 1 is so chosen that a clot 33 (not shown) forming on edge 3 is transversed by light beam 4. As the clot forms, it absorbs at least a portion of light beam 4 transmitted from light source 5. With the clot forming, the amount of light consequently received by light receiver 6 diminishes thus resulting in a change of the absorptance value measured with light beam 4 passing through the cuvette.

As shown in FIG. 1, the apparatus also contains a light source 62 (e.g. a light-emitting diode) and a light receiver 63 (e.g. a photodiode). With these components there is produced and, respectively, received a beam of light 61 which passes through cuvette 1 above edge 3, in order to enable a measurement of the extinction of light of the cuvette content which is transversed by light beam 61. The path of light beam 61 through cuvette 1 is so chosen that the maximum amount of sample introduced into the cuvette, is not detected by light beam 61, but that after the addition of a reagent, even in the case of the minimum volume chosen for the sample-reagent mixture, this mixture is transversed by light beam 61. When this amount of reagent is introduced into the cuvette, it mixes with the sample and absorbs at least a portion of light beam 61 transmitted from light source 62. The amount of light consequently received by light receiver 63 is diminished resulting in a change in the absorptance value measured with light beam 61 passing through the cuvette.

To reduce the influence of the ambient light on the absorptance measurements with light beams 4 and 61, there are preferably used photodiodes with a built-in infrared filter as light receivers. The filter range of the latter filter preferably is from about 900 to about 1000 nm and has a minimum attenuation at about 940 nm. With the filter, the sensitivity of the measurements to an ambient illumination with incandescent light is about 5 times smaller than without the filter.

Referring to FIG. 2, there is illustrated cuvette 1 and an arrangement 21. As shown in FIG. 2, chamber 7 in the upper part of cuvette 1 is connected via opening 9 with arrangement 21 with which a variable air pressure acting on the content of the cuvette can be produced. By means of this pressure, a sample-reagent mixture in the inventive apparatus is moved in the manner which is illustrated by FIG. 3(3). As described hereinafter with reference to FIGS. 7 and 8, arrangement 21 can contain, for example, a vibrating membrane 22 as a pump element. When cuvette 1 is empty or when its content does not reach the level of edge 3, air can freely flow around this edge and the air pressure produced with arrangement 21 passes through a conduit 23, through opening 9 into chamber 7, along one side of partition 2 in chamber 7, around edge 3, along the other side of partition 2 in chamber 8 and out opening 11 of cuvette 1. Opening 11 remains open in operation. In FIG. 2, light beams 4 and 61 are shown by circles.

As shown in FIG. 3, the following steps are carried out in performing the inventive method with the apparatus described above:

(1) Introducing the Sample

A predetermined volume of a blood or plasma sample 31 is introduced (e.g. pipetted) into the cuvette and incubated therein. As shown in FIG. 3, the amount of sample illustratively is preferably chosen so small that its level is below edge 3 and thus air can flow freely between the surface of the sample and edge 3. The air pressure produced by arrangement 21 (not shown) thus causes no movement of the sample which remains stationary as long as the predetermined amount of the reagent is not yet introduced into the cuvette.

(2) Introducing the Reagent

A predetermined volume of reagent is introduced (e.g. pipetted) into the cuvette. The respective volumes of sample and reagent are chosen so that the surface of sample-reagent mixture 32 lies in each case above the level of edge 3 and light beam 61. The following effects thus are achieved as soon as the reagent is introduced into the cuvette:

(3) Detecting the Initial Presence of the Sample-Reagent Mixture and Causing Movement of the Mixture Around the Edge The sample-reagent mixture is detected with light beam 61. This point in time marks the beginning of the measurement of the coagulation time and is registered with known electronic signal processing means. By the action of the above-mentioned air pressure from arrangement 21 upon the sample-reagent mixture, the mixture now flows and thereby moves back and forth between the positions (a) and (b) show in FIG. 3(3). The sample and the reagent thereby are mixed well together and a flowing of the mixture around sharp edge 3 of partition 2 in cuvette 1 is brought about.

(4) Detecting the Clot

By the relative movement of the mixture in relation to edge 3 (as shown in FIG. 3(3)), a clot 33 forms on edge 3 at the moment of the clotting. Since this clot is detected with the beam of light 4, a sudden and perceptible change in the absorptance value measured with light beam 4 results. By determining this change, the point in time of the coagulation and at the same time the end of the measurement of the coagulation time (and thereby the coagulation time), are clearly and precisely measured. For this determination and for recording the values ascertained, there are used known electronic signal processing or data recording means.

In a variant of the inventive method described above, and insofar as the measurement is not impaired thereby, the amount of sample can be chosen so large that the level of the sample alone in the cuvette lies above edge 3 but below the path of light beam 61. In this case, the sample is traversed by light beam 4 before the addition of reagent and the sample moves by the action of the air pressure of arrangement 21 mentioned above, in a manner analogously to that shown in FIG. 3(3) for the sample-reagent mixture. Upon the addition of the reagent into the cuvette, the sample-reagent mixture 32 causes a change of the absorptance value measured with light beam 61. This change due to the introduction of the reagent into the sample is detected and constitutes the beginning of the measurement of the coagulation time.

Although preferred, it is not necessary to introduce the sample into the cuvette before introducing the reagent. In a variant of the inventive method, the reagent is first added to the cuvette and then the sample is added. In this case, the level of the reagent alone may or may not be above edge 3. If the level of the reagent alone is lower than edge 3, light beam 61 would not detect the reagent and arrangement 21 would not cause the reagent to move. Upon adding the sample in an amount sufficient for the level of the resulting sample-reagent mixture to be above edge 3, light beam 61 would detect the presence of the mixture and thereby mark the beginning of the measurement of the coagulation time. If the level of the reagent alone is higher than edge 3, light beam 61 would detect the presence of the reagent alone by a change of the absorptance value measured with light beam 61. Upon adding the sample, there would be a further change in the latter absorptance value, this change thereby marking the beginning of the measurement of the coagulation time.

As shown in FIGS. 4a to 6b, the apparatus in accordance with the invention can also operate with a different embodiment of a cuvette.

FIG. 4a shows a front cross-sectional view of a cuvette 41 and FIG. 4b shows its end view. As in the case of cuvette 1 of FIG. 1, cuvette 41 also has a partition 44 with a sharp edge 43. Partition 44 divides the cuvette into two chambers. A top 45 of cuvette 41 is open.

As shown in FIG. 5, variable air pressure is supplied to cuvette 41 through a lateral opening 42 in one of the chambers of cuvette 41. Opening 42 is connected via a conduit 77 with an arrangement for producing variable air pressure. Cuvette 41 in FIGS. 4a–6b has the advantage that it can be easily placed in a measuring device or holder.

FIG. 6a shows cuvette 41 containing only the sample. FIG. 6b shows the cuvette 41 when it contains the sample-reagent mixture. In FIGS. 4a, 6a and 6b the position of the light beams 4 and 61, respectively, are each marked with a small circle.

The mode of operation of the apparatus in accordance with the invention with cuvette 41 of FIGS. 4a and 4b is the same as described above with reference to FIG. 3.

FIG. 7 illustrates a front cross-sectional view of an embodiment of the arrangement 21 (in FIG. 2) for producing variable air pressure. This arrangement is contained in a housing 71 having a membrane 72 which has a core of sheet steel 73 arranged in the housing. Oscillation of membrane 72 is brought about with an electromagnetic drive assembly which contains a magnetic core 74 and a magnetic coil 75 and to which is applied a suitable alternating current. In housing 71 there results a variable air pressure which is applied to two cuvettes of the inventive apparatus via conduits 77 and 78, respectively.

FIG. 8 shows schematically a typical variation with time of the air pressure which can be produced with the arrangement of FIG. 7. The air pressure varies between about +2 and about −2 millibar, and its variation with time has approximately the form of a sine wave with a frequency of about 40 Hz.

The working examples described above operate, for example, with a sample volume of about 100 or about 200 $\mu$l and with a fixed reagent volume of about 200 $\mu$l.

While the invention has been described in conjunction with certain embodiments, it is understood that various modifications and changes may be made without departing from the spirit and scope of the invention.

I claim:

1. An improved method for measuring the coagulation time of a blood sample in which a blood sample-reagent mixture is formed by introducing a sample and at least one reagent into a cuvette, which improved method comprises moving the sample-reagent mixture in the cuvette so that the mixture flows back and forth around a sharp edge formed by the intersection, by an acute angle, of opposite faces of a partition of the cuvette, said edge projecting into the cuvette, whereby a clot forms on this edge.

2. The method of claim 1 wherein the sample-reagent mixture is moved by air pressure.

3. The method of claim 1 wherein the beginning of the measurement of the coagulation time is determined by detecting a change in absorptance value measured with a first beam of light passing through the cuvette at a location above the edge and approximately adjacent the partition, the change in the absorptance value occurring as a result of the addition of the reagent to the blood sample.

4. The method of claim 3 wherein the formation of the clot is determined by detecting a change in absorptance measured with a second beam of light which passes through the blood sample-reagent mixture in the cuvette close to and below the edge.

5. A method for measuring the clotting time of a blood sample with an apparatus including a cuvette for receiving a blood sample and at least one reagent which thereby form a sample-reagent mixture, said cuvette having an upper portion divided into two chambers by a partition therein and having a bottom, the partition having opposing faces and a sharp wedge-shaped edge portion formed by the intersection, at an acute angle, of such opposing faces of the partition and situated within the cuvette at a predetermined distance from the bottom of the cuvette to permit unobstructed communication of said blood sample-reagent mixture between the two chambers and to permit flow of the blood sample-reagent mixture from one chamber to the other around the edge portion when variable air pressure is applied to the cuvette thereby causing a clot to form on said edge portion; one of the chambers being connected via an opening with means for producing variable air pressure to effect movement of the blood sample-reagent mixture from one chamber to the other around the edge portion, the method comprising:
(a) introducing the blood sample into the cuvette;
(b) introducing the reagent into the cuvette, the resulting blood sample-reagent mixture having a height above the edge of the partition in relation to the bottom of the cuvette;
(c) detecting the point of time at which the blood sample-reagent mixture is formed by means of a first light beam which passes through the cuvette, above the edge portion approximately adjacent the partition;
(d) introducing varying air pressure into the chamber of the upper portion of the cuvette which is connected to the variable air pressure means, thereby causing the blood sample-reagent mixture to flow back and forth around said edge portion and form a clot on said edge portion; and
(e) detecting the point of time at which the clot is formed by means of a second light beam which passes through the cuvette, close to and below the edge portion.

* * * * *